United States Patent [19]

Warpehoski

[11] Patent Number: 4,590,280
[45] Date of Patent: May 20, 1986

[54] PREPARING INDOLINE DERIVATIVES

[75] Inventor: Martha A. Warpehoski, Kalamazoo, Mich.

[73] Assignee: The Upjohn Company, Kalamazoo, Mich.

[21] Appl. No.: 712,307

[22] Filed: Mar. 15, 1985

[51] Int. Cl.[4] ........................................... C07C 209/12
[52] U.S. Cl. .................................................... 548/491
[58] Field of Search ................ 548/491; 564/417, 418; 555/445

[56] References Cited

U.S. PATENT DOCUMENTS 4,169,888 10/1979 Hanka et al. ......................... 424/121
4,424,365 1/1984 Wierenga ............................. 548/421

OTHER PUBLICATIONS

D. G. Martin, C. G. Chidester, D. J. Duchamp and S. A. Mizsak, *J. Antibiot.*, 33, 902 (1980), "Structure Proof of Antibiotic CC-1065".

Primary Examiner—Donald G. Daus
Assistant Examiner—Mary E. Ceperley
Attorney, Agent, or Firm—John T. Reynolds

[57] ABSTRACT

An improved process for preparing sulfonylated indoline compounds of the formula

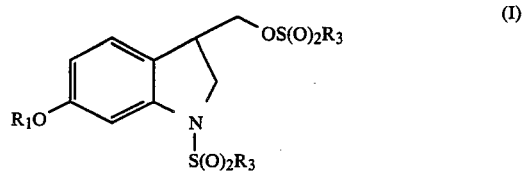

via reduction of a nitrodiol of the formula

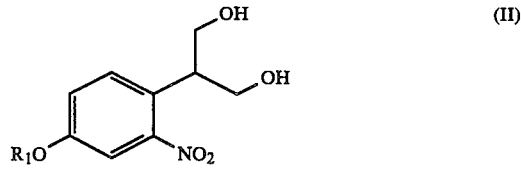

where $R_1$ and $R_3$ are defined in the specification, to obtain the corresponding aminodiol

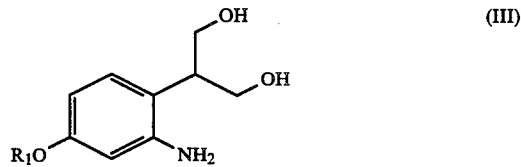

and then the aminodiol (III) is sulfonylated and cyclized in situ to obtain the sulfonylated indoline compound (I). The substituted indoline compounds (I) are useful in overall processes for making 1,2,8,8a-cyclopropa[c]benzo[1,2-b:4,3-b']dipyrrol-4(5H)-ones which have useful light absorber, anti-bacterial and anti-tumor pharmaceutical use properties.

3 Claims, No Drawings

PREPARING INDOLINE DERIVATIVES

INTRODUCTION

This invention relates to a process for preparing substituted indoline compounds, which are useful as chemical intermediates in processes for preparing 1,2,8,8a-cyclopropa[c]benzo[1,2,b:4,3-b']dipyrrol-4(5H)-ones. More particularly, this invention provides an improved process for preparing sulfonylated indoline compounds, of formula (I) hereinbelow, which new process avoids sensitive intermediate compounds, and makes the process for making these sulfonylated indoline compounds more easily reproducible for scale up to commercial processing.

BACKGROUND OF THE INVENTION

Antibiotic CC-1065 is disclosed and claimed by its chemical and physical parameters in U.S. Pat. No. 4,169,888. Subsequently, the structure of antibiotic CC-1065 was elucidated as disclosed in "Structure Proof of Antibiotic CC-1065", D. G. Martin, C. G. Chidester, D. J. Duchamp, and S. A. Mizsak, *J. Antibiot.*, 33 902 (1980). Antibiotic CC-1065 consists of a three-fragment system with the most labile portion of the molecule being the fragment named 1,2,8,8a-cyclopropa[c]benzo[1,2-b:4,3-b']dipyrrol-4(5H)-one. Attempts to obtain this fragment by degradation of antibiotic CC-1065 have not been published.

Wierenga U.S. Pat. No. 4,424,365 discloses and claims compounds of the formula

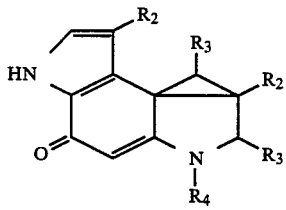

wherein $R_2$ and $R_3$ are H, alkyl of from 1 to 5 carbon atoms, inclusive, and phenyl; $R_4$ is selected from the group consisting of $SO^2R_2$, $SO_2CH_2$—COphenyl, $CO_2CH_2Z$ where Z is selected from the group consisting of $CH_2I$, $CCl_3$, $CH_2SO_2R_2$, phenyl, and fluorenylmethyl.

The Wierenga '365 patent also discloses in Chart 2 thereof a multi-step process for preparing 1,2,8,8a-cyclopropa[c]benzo[1,2-b:4,3-b']dipyrrol-4(5H)-one compounds, starting from 2-chloro-5-(oxy-ether)nitrobenzene. That process proceeds from the above-substituted nitrobenzene through the first step-aromatic nucleophilic substitution (replacing the 2-chloro group), followed by a reduction step (Step 2) to form the 2-[bis(hydroxymethyl)methyl]-5-(oxy-ether)-nitrobenzene (3). In Step 3 of Chart 2 of the Wierenga '365 patent, the hydroxy groups are replaced with functional groups (funtional group interchange), for example, with mesylate or tosylate groups using the corresponding sulfonyl chloride with or without the presence of pyridine, with or without the presence of an inert solvent such as methylene chloride, or other acid acceptors such as a trialkyl-amine. Thereafter, in Step 4 of that '365 patent, Chart 2 process the nitro group is reduced to the amino group (not shown in the '365 patent) with concomitant intra-molecular cyclization to give an N—H (unsubstituted) indoline which is further reacted in situ to give the indoline (dihydro-indole) compound of the formula

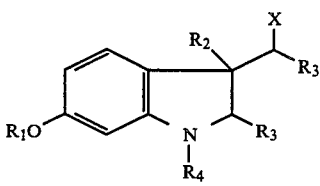

as shown in U.S. Pat. No. 4,424,365 from which compound (5) the therein disclosed process proceeds through several more steps to the therein desired 1,2,8,8a-cyclopropa[c]benzo[1,2-b:4,3-b']dipyrrol-4(5H)-one.

However, in further study of this overall process we have found that the above sulfonylated aminobenzene/intermediate compounds are somewhat unstable and are not as easy to work with when larger scale operation of the overall process is contemplated.

OBJECTS OF THE INVENTION

It is an object of this invention to provide an improved process for preparing sulfonylated indoline compounds through intermediates which are more stable and more reproducible in consistent yield processing than the prior art sulfonylated aminobenzene compounds.

Other objects, aspects and advantages of this process improvement invention, and the products of the claimed process will be apparent from the remaining specification and the claims which follow.

SUMMARY OF THE INVENTION

Briefly, it has been found according to this invention that the overall process for making 1,2,8,8a-cyclopropa[c]benzo[1,2-b:4,3-b']dipyrrol-4(5H)-one end products can be made easier, by avoiding the production of sensitive or unstable intermediate compounds in the process and by conducting the process through the production of more consistently reproducible intermediates for anticipated scale-up operations.

We have discovered that if the nitrodiol (II) is first reduced to the aminodiol (III), before the anilino-amino-hydrogen and hydroxy groups are sulfonylated, in the production of the bicyclic bis-sulfonylated indoline derivative intermediate compounds (I) (compound 5 in Chart 2 of U.S. Pat. No. 4,424,365), the process avoids the production of the reaction sensitive and hard to handle 2-[(bis-sulfonylated-methyl)methyl]-5-(ether group)-aminobenzene type compounds (VIIb) hereinbelow, or the cyclized intermediate (VIIa).

DETAILED DESCRIPTION OF THE INVENTION

Reading of this specification presumes the reader has a copy of U.S. Pat. No. 4,424,365.

This invention is to an improved process for preparing the substituted indoline compounds (I—see General Formula Sheet) wherein $R_1$ is selected from the group consisting of methyl, benzyl, allyl, methylthiomethyl, methoxymethyl, methoxyethoxymethyl, 2,2,2-trichloroethyl or —$CH_2CH_2Si(R_2)$ where $R_2$ is $C_1$ to $C_5$-alkyl or phenyl;

$R_3$ is $C_1$ to $C_5$-alkyl, phenyl or benzyloxymethyl, which comprises (a) reducing a nitrodiol compound of formula II (see General Formula Sheet) to form the aminodiol compound of formula III under known nitrobenzene to aniline reduction conditions, e.g., as described in step (4), column 2, of U.S. Pat. No. 4,424,365, and (b) reacting the aminodiol (III) from step (a) hereinabove with a sulfonylation reactant compound (IV) (see General Formula Sheet) where $R_3$ is as defined hereinabove, in an amount of sulfonylation reactant (IV) sufficient to sulfonylate the anilino-amino nitrogen and the hydroxy groups, in the presence of an acid absorbing base, with or without the presence of an inert solvent or diluting liquid such as a non-polar liquid, e.g., methylene chloride, while cooling the liquid mixture to a temperature low enough to control the speed of the reaction and to smoothly effect in situ cyclization of the sulfonylation aniline to form the sulfonylated indoline compound (I).

The resulting sulfonylated indoline compound (I) can then be processed further in the overall process outlined in Chart 2 of U.S. Pat. No. 4,424,365, starting from compound (5) thereof to the 1,2,8,8a-cyclopropa[c]benzo[1,2,6:4,3-b']dipyrrol- end product (12) thereof.

In step (a) of the process improvement of this invention, the preferred nitro group reducing conditions involve the use of hydrogen under pressure in the presence of a platinum oxide catalyst and in the presence of a $C_1$ to $C_8$-alkanol, e.g., ethanol or an N,N—$C_1$ to $C_8$-dialkylacylamide, e.g., N,N-dimethylformamide (DMF) N,N-diethylformamide, N,N-dimethylacetamide (DMAC), and the like, or in the presence of a tertiary amine such as pyridine, trimethylamine, triethylamine, tripropylamine, N,N-dimethylaniline or the like. Alternately, known forms of palladium and nickel hydrogenation catalysts can be substituted for the platinum oxide. Alternate reducing conditions can involve the use of iron metal or titanium trichloride or stannous chloride in acid media to effect reduction. Conventional hydrogenation apparatus can be used. The reduction reaction is usually essentially complete in from 1 to 3 hours depending upon the concentrations of the reactants, hydrogen pressure conditions, the temperature, and other conditions of concern to the operating chemist.

Upon completion of the reduction, the reaction mixture can be treated in a conventional manner, e.g., by filtration, to separate any solid and catalyst materials from the liquid mixture containing the amino-diol. The used catalyst can be washed with an amino-diol solvent to recover any amino-diol therefrom. The filtrate, any catalyst wash liquid, can be combined and treated to recover the amino-diol therefrom. For example, any diluting solvent or inert diluent can be evaporated off, under conventional vacuum procedures to leave as residue the crude aminodiol intermediate product (III), and then purified, if desired, e.g., one or more re-crystallization procedures or by chromatography procedures. However, in plant operation procedures it may be desired to carry an amino-diol compound solution, e.g., in pyridine, into the next step of the process without further purification or crystallization, although samples of the reaction mixture may be taken, purified and analyzed to check on yields and quality of the intermediate product.

In the sulfonylation/cyclization step (b) of the process, a solution or mixture of the amino-alcohol in a diluting liquid or solvent such as a tertiary amine, e.g., pyridine, or a non-polar inert liquid diluent, e.g., methylene chloride, or the like, is preferably cooled to a temperature low enough to control the speed of the reaction which is to follow, and then mixed, preferably gradually, e.g., dropwise or portionwise mixing, with the selected $R_3$—$S(O)_2$—X reactant IV, in an amount sufficient to smoothly effect the sulfonylation and resulting in situ cyclization to form the substituted indoline product of the process (I). A molar excess of the reactant IV (relative to the three possible reaction sites on the amino diol reactant III) to ensure the formation of essentially the single product (I). If less sulfonylation reactant (IV) is used (i.e., a molar equivalent deficiency) other yield lowering sulfonylated intermediates of the formulas (V) and (VI) (see General Formula Sheet) are formed, remain in the mixture and complicate the single product (I) recovery from the reaction mixture. Thus, it is preferred to use a reasonable excess over 3 molar equivalents of the sulfonylation reactant IV, relative to the amino-diol reactant (III), to ensure complete reaction.

This process improvement reaction procedure is preferred over the procedure described in U.S. Pat. No. 4,424,365, since with this new process improvement procedure, no reactive intermediates such as compounds of formula (VIIa and VIIb) are formed, thus making the overall yields better, and the overall process simpler to operate.

Examples of sulfonylation reactants (IV) which can be used in this step (b) of this process improvement include the $C_1$ to $C_5$-alkylsulfonyl halides, phenylsulfonyl halides, tolylsulfonyl halides and benzyloxymethylsulfonyl halide, where the halide is a halide having an atomic number of from 9 to 35, namely, fluoride, chloride or bromide. For reasons of practical economy the chlorides or bromides would most probably be used. The chlorides are preferred for reasons of cost and availability. Specific examples include:

methanesulfonyl chloride or bromide,
ethanesulfonyl chloride or bromide,
n-propylsulfonyl chloride or bromide,
isopropylsulfonyl chloride or bromide,
n-, iso- and tert-butylsulfonyl chlorides and bromides,
n-, iso- and tert-pentylsulfonyl chlorides and bromides,
phenylsulfonyl chloride or bromide,
p-tolylsulfonylchloride or bromide,
benzyloxymethyl chloride or a bromide, and commercially available forms and mixtures containing these reactants.

When the mixing of the aminodiol (III) and sulfonylation reactant (IV) is essentially completed, the mixtures can be stirred or otherwise agitated in the cold (say, at about 0° C. to about +5° C.) and then at room temperature, if desired, for a time sufficient to ensure complete reaction, and the reaction mixture can be treated or 'worked up' by conventional means to recover the desired substituted indoline product (I) from the resulting reaction mixture.

We prefer to quench the reaction mixture with cold water, for example, by adding ice to the reaction mixture, or by cooling the reaction vessel to at least about +5° C. or lower and adding water, to hydrolyze any excess sulfonylation reactant to give a water soluble sulfonic acid. The organic solvents (e.g., a $C_1$ to $C_3$-alkyl-$C_2$ to $C_4$-carboxylate, e.g., methyl acetate, ethyl acetate, propyl acetate, propyl propionate, butyl acetate, or the like, alone, or mixed with a diluting organic liquid such as a dialkyl ether, such as diethyl ether, dipropyl ether, or commercially available mixture equivalents thereof) are added to dissolve the substituted indoline product (I) therein to separate it from the water soluble, hydrolyzed sulfonylation reactant.

The organic solvent/substituted indoline product (I) solution can then be separated from the residual aqueous reaction mixture and purified by washing with a number of aqueous wash solutions to separate salt, acid solvent and sulfonylation reactant impurities. Such wash liquids can include water, acid solutions such as dilute hydrochloric acid solution, and saturated solutions of salts such as sodium bicarbonate, sodium chloride, and the like. The organic liquid phase containing the product (I) can then be separated from the aqueous phase and dried with conventional solution drying agents such as anhydrous sodium sulfate, the solution can be concentrated, and the product (I) containing residue can be purified by a number of known available methods such as re-crystallization or by chromatography of the crude product I through silica gel columns using polar/non-polar solvent mixtures, and then more pure polar solvents which are effective for effecting fractional separation of the desired product (I) from undesired impurities. We have found that mixtures of 50:50 V/V mixtures of ethylacetate:hexane, followed by greater proportions of ethyl acetate, to essentially only ethyl acetate are effective eluent liquids for isolating analytical sample quality product (I) materials, resulting from the process improvement of this invention.

As indicated above, the product (I) of the process of this invention are useful as chemical intermediates in a larger chemical process for making valuable 1,2,8,8a-cyclopropa[c]benzo[1,2-b:4,3-b']dipyrrol-4(5H)-one compounds referred to in U.S. Pat. No. 4,424,365. The product (I) here can be used as the compound product-/reactant (5) in Chart 2 shown in column 12 of that '365 patent disclosed process.

The invention is further exemplified by the following detailed example, which is not intended to be limiting. All temperatures are in degrees Centigrade unless otherwise indicated.

EXAMPLE 1

Step 1 NITRODIOL REDUCTION TO AMINODIOL

To 13.9 g., (46 millimoles) of the nitrodiol, 2-[bis(hydroxymethyl)methyl]-5-benzyloxy-nitrobenzene, in 500 ml. of absolute ethanol there was added 1.4 g. of platinum oxide. The mixture was placed under 30 to 35 psig pressure of hydrogen with shaking for two hours. Then another 1.4 g. of platinum oxide was added and hydrogenation was continued for two hours. The mixture was filtered through a filter aid, Celite ®, and the filtrand (filtered solids) was washed separately with 100 ml. of ethanol and then with 300 ml. of N,N-dimethylformamide (DMF). The resulting DMF solution was concentrated to 10 g. of a yellow solid consisting (by Nuclear Magnetic Resonance (NMR) spectral analysis) of 2.1 g. of DMF and 7.9 g. of the aminodiol 2-[bis(hydroxymethyl)methyl]-5-benzyloxyaniline (29 millimoles, 63 percent yield).

The above ethanol wash liquid was concentrated to 4.3 g. of a brown solid which was chromatographed on a column containing 40 g. of silica gel, eluting the solid on silica gel column with 1 liter of 30 percent V/V acetone in methylene chloride mixture and then with 600 ml. of acetone, to yield an additional 1.55 g. (5.7 millimoles, 12 percent yield) of the above pure aminodiol. A portion of this aminodiol was recrystallized from acetone to yield an analytical sample, m.p. 149°–151° C. of off-white crystals.

NMR (DMSO-d$_6$): 7.43 (m, 5H); 6.88 (d, 1H, J=8 Hz); 6.34 (d, 1H, J=2 Hz); 6.22 (dd, 1H, J=2, 8 Hz); 5.0 (s, 2H); 4.84 (brs, 2H, NH); 4.48 (t, 2H, J=5 Hz, OH); 3.6 (m, 4H); 2.8 (t, 1H, J=6 Hz)

Analysis: Calcd. for C$_{16}$H$_{19}$NO$_3$: Calcd.: C: 70.30; H: 7.01; N: 5.13; Found: C: 70.32; H: 7.13; N: 5.13

MS: Calcd.: 273.1365; Found: 273.1358

Step 2 SULFONYLATION AND CYCLIZATION

The total crude aminodiol, 2-[bis(hydroxymethyl)methyl]-5-benzyloxyaniline, obtained from the catalytic hydrogenation of 11 millimoles of the nitrodiol, as described in Step 1 hereinabove, was dissolved in 55 ml. of pyridine under nitrogen and cooled in an ice-water bath. To this solution, there was added, dropwise, 3.0 ml. (39 millimoles) of methanesulfonyl chloride. The resulting reaction mixture was stirred at 0° C. for 0.5 hours and quenched with ice to essentially destroy excess methanesulfonyl chloride and diluted with 250 ml. of ethyl acetate and 50 ml. of diethyl ether. The organic liquid phase was separated from the aqueous phase and washed with water, three times with 1.2N hydrochloric acid solution, twice with saturated sodium bicarbonate solution and once with saturated sodium chloride solution. The solution was dried with sodium sulfate, concentrated and chromatographed on 200 g. of silica gel, using first 50 percent V/V ethyl acetate/hexane and then ethylacetate as eluent liquids to separate out and recover 2.3 g. (5.6 millimoles, 51 percent yield, based upon the nitrodiol starting material) of the 2,3-dihydro-6-benzyloxy-1-(methylsulfonyl)-1H-indole-3-methanol, methane sulfonate ester.

NMR (acetone-d$_6$): 7.4 (m, 6H); 7.12 (d, 1H, J=2 Hz); 6.75 (dd, 1H, J=2, 8 Hz); 5.14 (s, 2H); 4.4 (m, 2H); 4.18–3.85 (m, 3H); 3.08 (s, 3H); 2.95 (s, 3H).

EXAMPLE 2

This example illustrates a larger scale operation of the process of this invention.

Step 1 NITRODIOL REDUCTION TO AMINODIOL

This procedure uses a 30-gallon stirred autoclave, a pressure filter and a 100 gallon glass reactor/receiver.

A solution of 2042 g. (6.74 mol) of the nitrodiol (U-69,798), 2-[bis(hydroxymethyl)methyl]-5-benzyloxy-nitrobenzene, in 19 gallons of methanol is hydrogenated at 50 psig over 200 g. of platinum oxide for 2.5 hours. The reaction mixture exotherms from 25° C. to 40° C. the reaction mixture is then cooled with cold water (18° C.) in the reactor jacket.

When the nitro group to amino group reduction reaction is complete, (as confirmed by thin layer chromatography (TLC) on silica gel using 25 percent V/V acetone in methylene chloride for development, R$_f$ for the nitrodiol is 0.4) the reaction mixture is filtered through a filter aid (Solka-Floc ™) on a pressure filter. Solka-Floc ™ is a trademark of James River Corporation.

The resulting drained reaction vessel and the filter cake are washed well with 25 gallons of methanol. The filter cake is rinsed again with 5 additional gallons of methanol.

The resulting filtrate liquid is concentrated (jet vacuum/35° jacket water) to near dryness and the resulting crystals of the aminodiol intermediate, 2-[bis(hydroxymethyl)methyl]-5-benzyloxyaniline, are collected and are washed with cold (0°-5° C.) methanol.

The resulting aminodiol intermediate product is dried to obtain about 1221 g. (66 percent yield of the aminodiol intermediate, having a melting point of 152° C.-154° C.).

Step 2 SULFONYLATION AND CYCLIZATION

In a 22 liter three-necked flask there is dissolved 1036 g. of (U-69,799) 2-[bis(hydroxymethyl)methyl]-5-benzyloxyaniline, prepared as described in Step 1 hereinabove, in 14.3 liters of pyridine under a nitrogen atmosphere.

The resulting solution is cooled to 0° C.

With stirring at 0° C., there is added 1087 ml. of methanesulfonyl chloride over a 30-minute period. Exotherms to as high as 23° C. are noted.

The resulting reaction is followed by TLC procedures using 25 percent acetone in methylene chloride ($R_f$ of the 2,3-dihydro-6-benzyloxy-1-(methanesulfonyl)-1H-indole-3-methanol, methane sulfonate product is 0.3). This reaction requires about 85 minutes for completion.

When the reaction is complete, as shown by TLC analysis of samples of the mixture, an equal volume of ice is added to quench the reaction by converting any excess methanesulfonyl chloride therein to the methanesulfonic acid.

The quenched reaction is then diluted with 28.6 liters of ethyl acetate. The resulting diluted organic/aqueous reaction mixture is extracted with 57.2 liters of 3N hydrochloric acid. The aqueous layer is separated and extracted with 2.9 liters of ethyl acetate. The main organic liquid phase, containing the desired product, is extracted with 5.7 liters of 1N hydrochloric acid solution.

The aqueous (hydrochloric acid) layer resulting from the immediately above main organic layer extraction is extracted with the organic layer resulting from the 2.9 liters of ethyl acetate extraction above.

The main organic layer, separated from the aqueous hydrochloric acid extraction wash, is then extracted with 28.6 liters of 5 percent W/V sodium bicarbonate in water solution.

The resulting aqueous liquid layer from the bicarbonate solution wash, is extracted with the organic (ethyl acetate containing) liquid wash from above.

The main organic liquid layer is extracted with 5.7 liters of saturated aqueous sodium chloride solution.

The resulting organic liquid layers, containing product, are combined and dried with anhydrous sodium sulfate.

The dried organic liquid, product-containing phase, is then concentrated to a purple gum residue, which residue is dried in vacuo at room temperature to constant weight to afford 1595.5 g. of crude 2,3-dihydro-6-benzyloxy-1-(methanesulfonyl)-1H-indole-3-methanol, methanesulfonate ester.

GENERAL CHEMICAL STRUCTURES

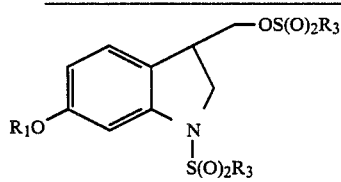
(I)

-continued
GENERAL CHEMICAL STRUCTURES

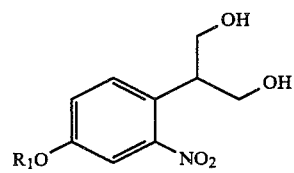
(II)

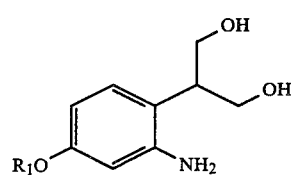
(III)

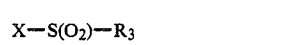
$X-S(O_2)-R_3$ (IV)

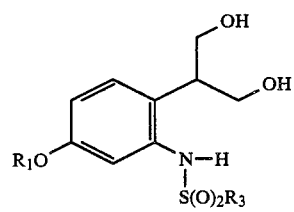
(V)

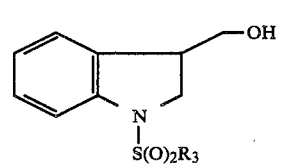
(VI)

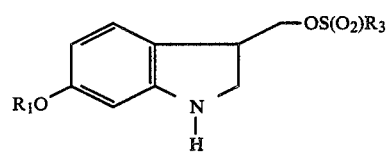
(VIIa)

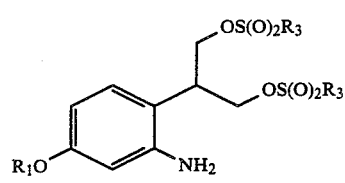
(VIIb)

I claim:
1. A process for preparing a substituted indoline compound of the formula

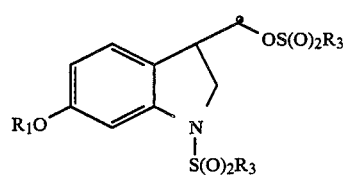
(I)

wherein $R_1$ is selected from the group consisting of methyl, benzyl, allyl, methylthiomethyl, methoxymethyl, methoxyethoxymethyl, 2,2,2-trichloroethyl and $-CH_2CH_2Si(R_2)_3$ where $R_2$ is $C_1$ to $C_5$-alkyl, or phenyl;

each $R_3$ is selected from the group consisting of $C_1$ to $C_5$-alkyl, phenyl, tolyl and benzoylmethyl, which comprises (a) reducing a nitrodiol compound of the formula

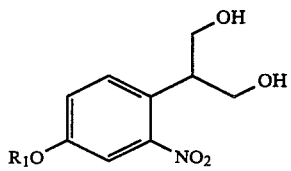 (II)

under hydrogenation conditions in the presence of a hydrogenation/reduction catalyst for a time sufficient to form an aminodiol compound of the formula

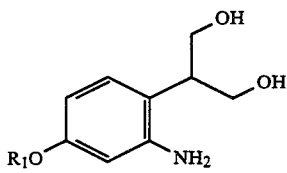 (III)

(b) reacting the aminodiol compound from step (a) with a sulfonylation reactant compound of the formula

 (IV)

where X is a halide having an atomic number of from 9 to 35, and $R_3$ is as defined hereinabove in an amount of the sulfonylation reactant (IV) sufficient to sulfonylate an anilino-amino hydrogen and the hydroxymethyl groups, of the aminodiol (III), in the presence of an acid absorbing base and to effect cyclization of the resulting sulfonylated intermediate so as to form the substituted indoline (I).

2. A process according to claim 1 wherein
$R_1$ is benzyl,
$R_3$ is $C_1$ to $C_5$-alkyl; and
X is halogen having an atomic number of from 9 to 35, so that the process produces a substituted indoline compound of the formula

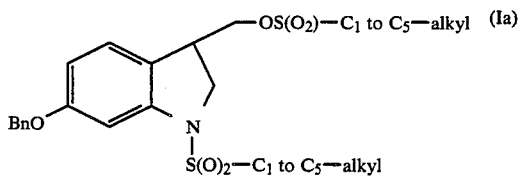 (Ia)

where Bn is benzyl.

3. A process according to claim 2 wherein
$R_1$ is benzyl,
$R_3$ is methyl, and
X is chloro
so that the process produces a compound of the formula

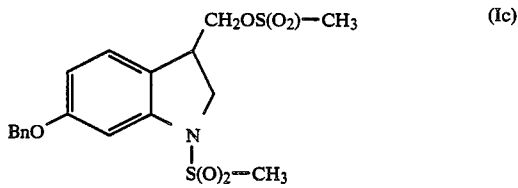 (Ic)

* * * * *